United States Patent [19]

Kaplan et al.

[11] Patent Number: 5,571,924
[45] Date of Patent: Nov. 5, 1996

[54] PROCESS FOR THE PREPARATION OF BENZOTRIAZOLES

[75] Inventors: Jere K. Kaplan, Mobile, Ala.; Wolfgang J. Tritschler, Bad Säckingen, Germany; Gary Clauson, San Diego, Calif.

[73] Assignee: Ciba-Geigy Corporation, Tarrytown, N.Y.

[21] Appl. No.: 501,638

[22] Filed: Jul. 12, 1995

[51] Int. Cl.$^6$ .................................................. C07D 249/18
[52] U.S. Cl. ............................................ 548/260; 548/259
[58] Field of Search ...................................... 548/259, 260

[56] References Cited

U.S. PATENT DOCUMENTS

| | | | |
|---|---|---|---|
| 3,978,074 | 8/1976 | Jancis | 260/308 |
| 4,219,480 | 8/1980 | White et al. | 548/260 |
| 4,230,867 | 10/1980 | Kintopf et al. | 548/260 |
| 4,999,433 | 3/1991 | Prestel et al. | 548/260 |
| 5,276,161 | 1/1994 | Prestel et al. | 548/260 |

FOREIGN PATENT DOCUMENTS

| | | |
|---|---|---|
| 0380840 | 8/1990 | European Pat. Off. |
| 0380839 | 8/1990 | European Pat. Off. |

OTHER PUBLICATIONS

Chemical Abstract 111:214490u & 111:214491v, 1989.
Chemical Abstract 117:191853x of JP 04,159,267, Jun. 1992 (1989).
Organic Syntheses, vol. 67, pp. 187–192, 1988.
Chemical Abstract 117:251972x of JP 04,193,869, Jul. 1992.
Chemical Abstract 89(21):180008c of JP 53063379, Jun. 1978.

*Primary Examiner*—Patricia L. Morris
*Attorney, Agent, or Firm*—Michele A. Kovaleski

[57] ABSTRACT

2-(2-Hydroxyphenyl)-2H-benzotriazoles can be prepared particularly advantageously by catalytically reducing a suitable o-nitroazobenzene compound to the corresponding N-oxybenzotriazole compound in the presence of hydrazine hydrate, a metal catalyst selected from the group consisting of Raney-Ni and the noble metals, an organic or inorganic base, an organic solvent, and optionally water; followed by isolating said N-oxybenzotriazole compound and converting it to the corresponding 2-(2-hydroxyphenyl)-2H-benzotriazole.

25 Claims, No Drawings

PROCESS FOR THE PREPARATION OF BENZOTRIAZOLES

The present invention relates to a two-step process for the preparation of 2-(2-hydroxyphenyl)-2H-benzotriazoles, first by catalytic reduction of suitable o-nitro-phenylazohydroxyphenyl compounds to the corresponding N-oxybenzotriazole compound in the presence of hydrazine hydrate, a metal catalyst and a base and isolation thereof, followed by subsequent conversion to the 2-(2-hydroxyphenyl)-2H-benzotriazole compound.

2-(2-Hydroxyphenyl)-2H-benzotriazoles are known from the literature as valuable UV light absorbers. They are widely used in practice as light stabilizers for a large number of substrates, such as, for example, thermoplastics, coating materials (such as varnishes), various recording materials (such as photographic layers and papers and printing inks and printing papers), textiles, and the like.

In accordance with the importance of these compounds, an extremely large number of processes for their preparation have already been proposed. The majority of said processes start from the above mentioned o-nitrophenylazo compounds and utilize reductive cyclization by various methods. One of these methods is catalytic hydrogenation, which has been described in a series of publications for the benzotriazoles mentioned.

For example, U.S. Pat. No. 3,978,074 describes a hydrogenation process of the abovementioned type which is carded out in alkaline and preferably in aqueous medium and in which the conventional noble metal and other metal catalysts are used as hydrogenation catalysts. According to U.S. Pat. No. 4,230,867, the hydrogenation is likewise carded out in a purely aqueous alkaline or aqueous/organic medium. The hydrogenation catalysts used are noble metals, and the hydrogenation process is carded out in organic solvents with the use of organic amines as bases. U.S. Pat. No. 4,219,480 teaches the use of a nickel catalyst as the hydrogenation catalyst.

CA 89(21):18008c, 111(23):214491v and CA 117:251972 are directed to another method of producing 2-(2-hydroxyphenyl)-2H-benzotriazoles by employing hydrazine hydrate as a reducing agent. CA 89(21):18008c relates to preparing benzotriazoles by alkaline or neutral reduction of a nitroazo benzene compound using hydrazine hydrate and no catalysts. CA 111(23):214491v is directed to the use of hydrazine hydrate in the presence of an organic hydrogen transfer catalyst and a base.

Surprisingly, it has now been found that 2-(2-hydroxyphenyl)-2H-benzotriazoles can be prepared in accordance with the instant invention in unexpectedly higher yields and quality than achieved hitherto by known processes. Further, much lower, and hence much safer, reaction temperatures can be used in accordance with the instant process to obtain the intermediate N-oxybenzotriazole compounds employing hydrazine hydrate than hitherto known, which is particularly advantageous to large scale industrial-type applications.

OBJECTS OF THE INVENTION

It is one object of the present invention to provide a novel method for preparing N-oxybenzotriazole compounds and 2-(2-hydroxyphenyl)-2H-benzotriazoles compounds in high yields and product quality.

Yet another object is to reduce the overall effluents and waste products as compared to existing processes, thereby achieving environmental benefits.

Still another object is to provide reaction products which allow 2-(2-hydroxyphenyl)-2H-benzotriazoles to be easily isolated and purified as target products.

Still other objects will become apparent from the discussion set forth hereinbelow.

DETAILED DESCRIPTION OF THE INVENTION

The instant invention relates to an improved process for the preparation of a 2-(2-hydroxyphenyl)-2H-benzotriazole of the formula I

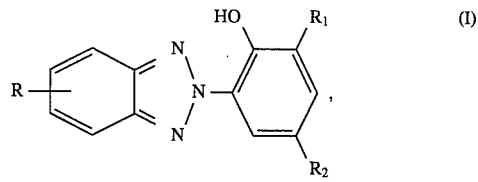

wherein
R is hydrogen, $C_1$-$C_{12}$alkyl, $C_1$-$C_4$alkoxy or halogen;
$R_1$ is hydrogen, $C_1$-$C_{24}$alkyl, $C_5$-$C_{12}$cycloalkyl, phenyl or phenyl-$C_1$-$C_9$alkyl;
$R_2$ is $C_1$-$C_{24}$alkyl, $C_5$-$C_{12}$cycloalkyl, phenyl, phenyl-$C_1$-$C_9$alkyl or a group —$C_nH_{2n}COOR_3$, in which n is 0 to 4 and $R_3$ is hydrogen or $C_1$-$C_{24}$alkyl or $R_2$ is —$(CH_2CH_2O)_xR_4$, in which x is 1 to 12 and $R_4$ is hydrogen or $C_1$-$C_{24}$alkyl, which process comprises the steps of a) catalytically reducing an azo compound of the formula II

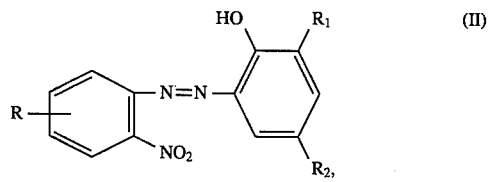

wherein R, $R_1$ and $R_2$ are as defined above, to an N-oxybenzotriazole compound of the formula III

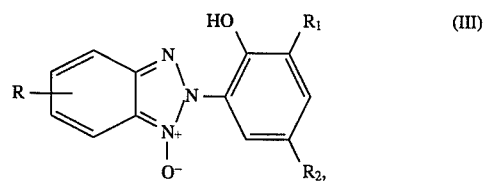

wherein R, $R_1$ and $R_2$ are as defined above, in the presence of an effective amount of hydrazine hydrate, a catalyst selected from the group consisting of Raney-Ni and the noble metals, an organic or inorganic base, an organic solvent, and optionally water, the reaction being carried out at temperatures between 15° and 60° C.;

b) isolating said N-oxybenzotriazole compound; and c) converting said isolated N-oxybenzotriazole compound to the corresponding benzotriazole compound of formula (I), wherein the improvement comprises catalytically reducing an azo compound of the formula II

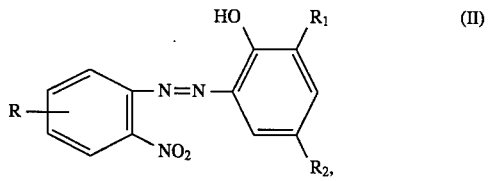

wherein R, $R_1$ and $R_2$ are as defined above, to an N-oxybenzotriazole compound of the formula III

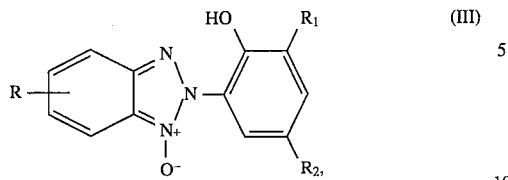

wherein R, $R_1$ and $R_2$ are as defined above, in the presence of an effective amount of hydrazine hydrate, a catalyst selected from the group consisting of Raney-Ni and the noble metals, an organic or inorganic base, an organic solvent, and optionally water, the reaction being carried out at temperatures between 15° and 60° C.

The instant invention further relates to an improved process for the preparation of an N-oxybenzotriazole compound of formula III

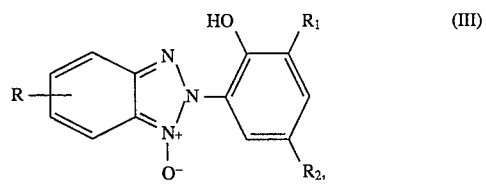

wherein

R is hydrogen, $C_1$-$C_{12}$alkyl, $C_1$-$C_4$alkoxy or halogen;

$R_1$ is hydrogen, $C_1$-$C_{24}$alkyl, $C_5$-$C_{12}$cycloalkyl, phenyl or phenyl-$C_1$-$C_9$alkyl;

$R_2$ is $C_1$-$C_{24}$alkyl, $C_5$-$C_{12}$cycloalkyl, phenyl, phenyl-$C_1$-$C_9$alkyl or a group —$C_nH_{2n}COOR_3$, in which n is 0 to 4 and $R_3$ is hydrogen or $C_1$-$C_{24}$alkyl or $R_2$ is —$(CH_2CH_2O)_xR_4$, in which x is 1 to 12 and $R_4$ is hydrogen or $C_1$-$C_{24}$alkyl, which process comprises the steps of a) catalytically reducing an azo compound of the formula II

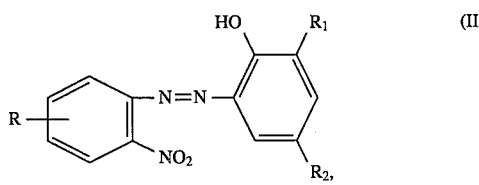

wherein R, $R_1$ and $R_2$ are as defined above, in the presence of an effective amount of hydrazine hydrate, a catalyst selected from the group consisting of Raney-Ni and the noble metals, an organic or inorganic base, an organic solvent, and optionally water, the reaction being carried out at temperatures between 15° and 60° C.

In formula I, $R_1$ and $R_2$ are, each independently of the other, preferably $C_1$-$C_{15}$alkyl or phenyl-$C_1C_4$alkyl and in particular α,α-dimethylpropyl, benzyl, phenethyl, α-methylbenzyl and α,α-dimethylbenzyl, in particular, α,α-dimethylpropyl, benzyl or α,α-dimethylbenzyl, and most particularly, α,α-dimethylpropyl. R is preferably hydrogen, $C_1$-$C_4$alkyl or halogen, in particular hydrogen, methyl or chlorine and most particularly hydrogen.

The starting compounds of formula II are known, for example from the publications mentioned at the beginning of EP-A 57,160, or they can be prepared by the methods mentioned them. For example, they can be prepared by diazotization of an o-nitroaniline of the formula

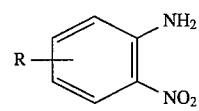

and coupling of the resulting diazonium salt onto a phenol of the formula

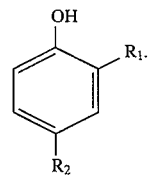

Compounds of the formula I in which R is hydrogen or $C_1$-$C_{12}$alkyl, in particular hydrogen, for example those compounds of formula I in which $R_1$ is hydrogen, $C_1$-$C_{15}$alkyl (in particular α,α-dimethylpropyl) or phenyl-$C_1$-$C_{15}$alkyl (in particular α,α-dimethylbenzyl) and $R_2$ is $C_1$-$C_{12}$alkyl (in particular $C_1$-$C_8$alkyl such as α,α-dimethylpropyl), phenyl-$C_1$-$C_3$alkyl (in particular α,α-dimethylbenzyl) or a group —$C_2H_4COOR_3$, in which $R_3$ is hydrogen or $C_1$-$C_{12}$alkyl (for example $C_1$-$C_8$alkyl), in particular hydrogen or $C_1$-$C_4$alkyl, are preferably prepared.

Of particular practical importance is the preparation of compounds of the formula I in which $R_1$ is hydrogen, $C_1$-$C_8$alkyl or α,α-dimethylbenzyl and $R_2$ is $C_1$-$C_8$alkyl or α,α-dimethylbenzyl. Of greatest importance are compounds of formula I wherein $R_1$ and $R_2$ are α,α-dimethylpropyl or α,α-dimethylbenzyl.

Hydrazine hydrate is a commercially available material and is employed, according to the invention, in an amount in the range of from about 50 to about 100%, preferably from about 50 to about 75%, even more preferably from about 55 to about 65%, and most preferably at about 60%, relative to the molar amount of o-nitroazobenzene compound used.

The hydrogenation catalysts used according to the invention are Raney-Ni or any of the noble metals on a support. Suitable supports are those customary in the technology of hydrogenation catalysts, for example carbon (for example activated carbon, charcoal, peat charcoal), kieselguhr, alumina, barium sulfate and the like. Carbon is preferred as support. Preferred catalysts according to the invention are Pt, Pd, Pt/Pd, Rh or Raney-Ni and most particularly, Pt/Id, Pd and Pt.

The amount of noble metal on the support (amount deposited) is in the range customary for hydrogenation catalysts. It is, for example, 0.1 to 10%, preferably 1 to 10% and most preferably 3 to 10%. Amounts of 3 to 7%, for example about 5%, in each case relative to the weight of the support material, are particularly advantageous.

The catalyst is advantageously used in an amount of about 0.1 to about 2%, preferably in the amount of about 0.3 to about 1.5% and most preferably in the amount of about 0.5 to about 1%, relative to the weight of the o-nitroazobenzene compound used. It will be appreciated that the catalyst is recyclable and recoverable, advantageously by filtration, if the process is carried out batchwise.

Both organic and inorganic bases can be used in the instant process. Suitable organic bases include any organic amine and in particular, a primary $C_2$-$C_{10}$alkylamine, a secondary $C_1$-$C_5$alkylamine, a tertiary $C_1$-$C_5$amine, an aliphatic amine, a cyclic amine, an aromatic amine and a heterocyclic amine. Preferably, the organic base is n-butylamine, diethylamine, pyrrolidine or pyridine.

Suitable inorganic bases include any inorganic bases, in particular sodium hydroxide, potassium hydroxide, sodium carbonate, sodium bicarbonate, potassium carbonate, potassium bicarbonate, barium hydroxide or lithium hydroxide. Most preferably, the inorganic base is sodium hydroxide.

It is of course possible to use mixtures of two or more of the organic or inorganic bases mentioned hereinabove in the process according to the invention.

The organic or inorganic base is present in the reaction mixture advantageously in an amount of about 10 to about 500%, preferably in the amount of about 100 to about 300% and most preferably in the amount of about 200 to about 250%, relative to the molar amount of the o-nitroazo compound used.

In the process according to the invention (if $R_3$ is not equal to hydrogen), an aromatic hydrocarbon, a halogenated aromatic hydrocarbon, a $C_1$-$C_{14}$alkyl alcohol, or a heterocyclic compound function as solvents. The reaction can optionally contain water, for example in amounts up to 200%, preferably less than or equal to 95%, relative to the total amount of solvent. Preferably, the solvent is a $C_1$-$C_{14}$alkyl alcohol such as methanol/water, ethanol, isopropanol or hexanol, or the solvent is preferably xylene, tetrahydrofuran or 2-butoxyethanol and most advantageously, methanol/water. Mixtures of the solvents mentioned herein can also be used.

If an azo compound of the formula II in which $R_2$ is $C_nH_{2n}$—COOH used as starting material, the reduction is carried out in water or a mixture of water and the above-listed solvents. In this case, the solvent system advantageously contains the amount of water necessary for dissolving the final product (in order to enable the catalyst to be separated off, for example by filtration), preferably at least 30%, in particular at least 50%, especially at least 70% of water.

The first stage of the process according to the invention can be carried out batchwise or continuously. For the continuous process, a fixed bed catalyst, is particularly suitable. In this case, the reaction mixture is removed continuously and fed with fresh nitroazo compound, hydrazine hydrate, amine and solvent.

A particularly advantageous variation of the process according to the invention, which allows a continuous process and leads to high conversions and short reaction times, consists of initially introducing the catalyst in a portion of the solvent into an autoclave and separately metering in the azo compound of the formula (ID and hydrazine hydrate, dissolved or dispersed in a further portion of the solvent, for example by means of a metering pump. The reaction solution can then be removed continuously, and the intermediate N-oxybenzotriazole product of the formula (HI) can be isolated therefrom in a conventional manner. Alternatively, it is also possible to filter off the catalyst in a batchwise process, and work up the filtrate correspondingly.

The first reduction stage of the instant process is advantageously carded out at temperatures of 15° to 60° C., in particular 20° to 60° C. and most particularly of from 25° to 55° C.

The isolation of the intermediate N-oxybenzotriazole product from the reaction medium is carded out by conventional means known to one skilled in the art. It varies, depending upon the type of solvent used. An advantageous method consists of precipitating the reaction mixture, which may have been concentrated before, by neutralization of the reaction mixture followed by filtration of the crystallized product. Work up and purification operations, if carried out, can be seen from the Examples.

Conversion of the isolated intermediate N-oxybenzotriazole of the formula (III) to the corresponding final benzotriazole product of formula (1) can be carded out by conventional means known in the art. The preferred method is hydrogenation, which is described, for example, in CA 111(23):21449v, U.S. Pat. No. 4,999,433 or U.S. Pat. No. 5,276,161.

As already mentioned, the 2-(2-hydroxyphenyl)-2H-benzotriazoles prepared in accordance with the instant invention are valuable UV absorbers which can be used in practice as light stabilizers for a large number of applications (such as those listed in the introduction). Descriptions of possible applications of the benzotriazoles are given in U.S. Pat. Nos. 3,055,896; 3,004,896; 3,072,585; 3,074,910; 3,189,615; and 3,004,194. The process according to the instant invention opens up an industrially particularly favorable and economical route for the preparation of benzotriazoles.

The following examples illustrate the process according to the invention in more detail and are not to be construed as limiting the scope of the instant invention in any way. Parts and percentages are by weight, unless stated otherwise.

Example 1

2-(2-Hydroxy-3,5-di-tert-amylphenyl)-2H-benzotriazole

To a reaction flask (equipped with a stirrer, nitrogen inlet, reflux condenser and thermometer) are charged 1000 g of a mixture of 130.0 g (0.330 moles) of 2-nitro- 2'-hydroxy-3', 5'-di-($\alpha,\alpha$-dimethylpropyl) azobenzene, 400 g of methanol and 380 g of water. (The remaining 90 g consists of sodium chloride and other by-products present in the reaction mixture resulting from preparation of the 2-nitro-2'-hydroxy-3', 5'-di($\alpha$, $\alpha$dimethylpropyl)azobenzene.) The reactor is heated to about 25° C., and 1.0 g of 8% Pd/2% Pt on activated carbon catalyst (about 50% water) is added. As the reaction is heated to 55° C. gradually over a period of one hour, 11.5 g of hydrazine hydrate is charged over a period of 30–35 minutes. After the temperature is maintained at 55° C. for one additional hour, the reaction mixture is analyzed for the starting azo compound by High Liquid Performance Chromatography, at which point there is present <0.3% of the starting azo compound. Thereafter, the reaction mixture is cooled to 35°–40° C., and the intermediate N-oxy compound is precipitated therefrom by adding hydrochloric acid to the reaction mixture until a pH of 8.0 is attained. The resulting N-oxy intermediate compound is filtered, washed with 150 g of methanol and dissolved in 220 g of xylene and 120 g of water at 60° C. The two-phase mixture is filtered to remove the catalyst and then separated to yield 97% (based on theory) of the corresponding intermediate N-oxybenzotriazole compound in solution with xylene.

The xylene solution containing the intermediate N-oxybenzotriazole compound is dried azeotropically and charged to a reactor purged with nitrogen and containing 0.8 g of 8% Pd/2% Pt on activated carbon catalyst (about 50% water). To the reactor are then charged n-butylamine (50 g) and hydrogen (50 psig). The reaction mixture is agitated at 50° C. for approximately two hours, at which time the catalyst is removed by filtration and the n-butylamine is removed by distillation. The xylene solution containing the product is extracted using 211.8 g of 78% sulfuric acid, and the title compound is crystallized using xylene/methanol, filtered and dried to yield 110.4 g (0.314 moles) of solid product (93% of theory), with a transmittance at 460 nm of greater than 97%.

Example 2

2-(2-Hydroxy-3,5-di-tert-amylphenyl)-2H-benzotriazole

Comparative Example

To a three-liter five-necked round bottomed flask (equipped as in Example 1 ) is charged 2-nitro-2'-hydroxy-3',5'-di-(α,α-dimethylpropyl)azobenzene ( 130.0 g, 0.339 mol) and xylene (200 g). The reaction mixture is heated to 80° C, followed by the addition of hydrazine hydrate over a period of 5 hours, after which time a temperature increase to about 110° C. is observed. After approximately three more hours of stirring at 110° C., some of the xylene is distilled from the reaction mixture such that a 50% solution remains. Methanol (360 g) is charged to the xylene solution at 60° C., and the intermediate N-oxybenzotriazole compound is crystallized by slowly cooling to 0° C., filtered and dried (yield: 90% based on theory).

This example shows that the use of hydrazine hydrate alone (i.e., in the absence of one of the instant metal catalysts) in a process otherwise comparable to the instant invention gives a yield of the intermediate N-oxybenzotriazole compound which is significantly lower than that obtained by the instant process.

Example 3

2-(2-Hydroxy-3,5-di-tert-amylphenyl)-2H-benzotriazole

Comparative Example

To a Parr reactor is charged 0.68 g of fresh 8:2 Pd:Pt on activated carbon catalyst and 2.71 g of recycled 8:2 Pd:Pt on activated carbon catalyst and 360.0 g of a mixture of 153.4 g (0.400 moles) of 2-nitro-2'-hydroxy-3'-5'-di-(α,α-dimethylpropyl)azobenzene and approximately 191 g of xylene (the remaining 15.6 g consists of organic impurities formed from the preparation of the starting azo compound), and 227.8 g of 90% assay n-butylamine (2.76 moles). The reaction mixture is cooled to 25°±2° C. while stirring, and the contents of the Parr reactor are blanketed with nitrogen. Hydrogen (20 psig) is charged to the unstirred Parr reactor and the system is allowed to equilibrate before resuming agitation. After the system has equilibrated, agitation is resumed, and the uptake of hydrogen is monitored. When the flow of hydrogen decreases to <80 scfm, the first half of the reaction (N-oxy formation) is complete. Agitation is stopped, and the reactor is pressured to 150 psig hydrogen. After the system equilibrates, agitation is resumed, while increasing the reaction temperature to 45±2° C. After the hydrogen flow drops to zero while at 45° C. and stirring at 600 rpm, the reaction mixture is held for an additional hour to ensure complete reduction. The hydrogen is vented off, the reactor is blanketed with nitrogen and the catalyst is removed from the reaction solution by filtration. The n-butylamine is distilled, and the product xylene solution is purified with a 282.4 g 78% $H_2SO_4$ wash, followed by two water washes. After azeotropically drying the purified reaction mass, the xylene solution is concentrated, and the product crystallized using methanol. The crystallization mixture is cooled to 0° C., filtered and dried to yield 123.0 g (0.350 moles) of a solid product (87% of theory), with a transmittance at 460 nm of about 97%.

This example shows that when hydrogenation (in the presence of one of the instant metal catalysts and a base) is used in a process otherwise comparable to the instant invention, a significantly lower yield of the title compound product (i.e. 87% of theory) is obtained than is achieved in accordance with the instant process, such as in Example 1 wherein 93% of theory is obtained.

Example 4

2-(2-Hydroxy-3,5-di-tert-amylphenyl)-2H-benzotriazole

The procedure of Example 1 is followed except that xylene is employed in the initial reaction, rather than methanol and water.

Example 5

2-(2-Hydroxy-5-methylphenyl)-2H-benzotriazole

The procedure of Example 1 is followed, except that an equivalent molar amount of 2-nitro-2'-hydroxy-5'-methylazobenzene is used instead of the azo compound used in Example 1.

Example 6

2-(2-Hydroxy-3,5-di-tert-butylphenyl)-2H-benzotriazole

The procedure of Example 1 is followed, except that an equivalent molar amount of 2-nitro-2'-hydroxy-3',5'-di-tert-butylazobenzene is used instead of the azo compound used in Example 1.

Example 7

2-(2-Hydroxy-5-tert-octylphenyl)-2H-benzotriazole

The procedure of Example 1 is followed, except that an equivalent molar amount of 2-nitro-2'-hydroxy-5'-tert-octylazobenzene is used instead of the azo compound used in Example 1.

Example 8

2-(2-Hydroxy-3-isobutyl-5-tert-butylphenyl)-2H-benzotriazole

The procedure of Example 1 is followed, except that an equivalent molar amount of 2-nitro-2'-hydroxy-3'-isobutyl-5'-tert-butylazobenzene is used instead of the azo compound used in Example 1.

Example 9

2-[(2-Hydroxy-3,5-di-(α,α-dimethylbenzyl)phenyl]- 2H-benzotriazole

The procedure of Example 1 is followed, except that an equivalent molar amount of 2-nitro-2'-hydroxy-3',5'-bis-α,α-dimethylbenzylazobenzene is used instead of the azo compound used in Example 1.

What is claimed is:

1. An improved process for the preparation of a 2-(2-hydroxyphenyl)-2H-benzotriazole of the formula I

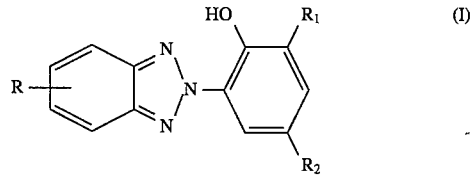

wherein

R is hydrogen, $C_1$-$C_{12}$alkyl, $C_1$-$C_4$alkoxy or halogen;

$R_1$ is hydrogen, $C_1$-$C_{24}$alkyl, $C_5$-$C_{12}$cycloalkyl, phenyl or phenyl-$C_1$-$C_9$alkyl;

$R_2$ is $C_1C_{24}$alkyl, $C_5$-$C_{12}$cycloalkyl, phenyl, phenyl-$C_1$-$C_9$alkyl or a group —$C_nH_{2n}COOR_3$, in which n is 0 to 4 and $R_3$ is hydrogen or $C_1$-$C_{24}$alkyl or $R_2$ is —$(CH_2CH_2O)_xR_4$, in which x is 1 to 12 and $R_4$ is hydrogen or $C_1$-$C_{24}$alkyl, which process comprises the steps of a) catalytically reducing an azo compound of the formula II

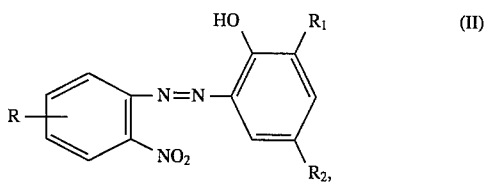

wherein R, $R_1$ and $R_2$ are as defined above, to an N-oxybenzotriazole compound of the formula III

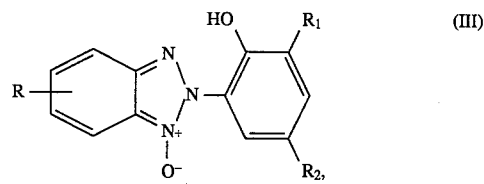

wherein R, $R_1$ and $R_2$ are as defined above, in the presence of an effective mount of hydrazine hydrate, a catalyst selected from the group consisting of Raney-Ni and the noble metals, an organic or inorganic base, an organic solvent, and optionally water, the reaction being carried out at temperatures between 15° and 60° C;

b) isolating said N-oxybenzotriazole compound; and c) converting said isolated N-oxybenzotriazole compound to the corresponding benzotriazole compound of formula (I), wherein the improvement comprises catalytically reducing an azo compound of the formula II

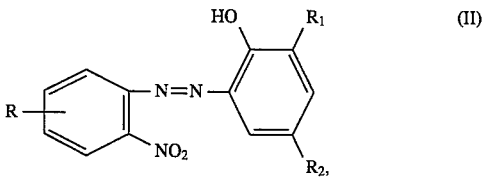

wherein R, $R_1$ and $R_2$ are as defined above, to an N-oxybenzotriazole compound of the formula III

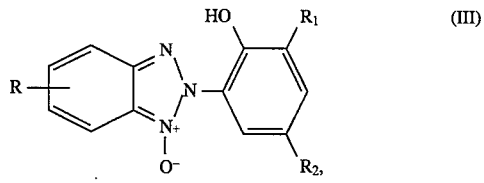

wherein R, $R_1$ and $R_2$ are as defined above, in the presence of an effective amount of hydrazine hydrate, a catalyst selected from the group consisting of Raney-Ni and the noble metals, an organic or inorganic base, an organic solvent, and optionally water, the reaction being carded out at temperatures between 15° and 60° C.

2. A process according to claim 1, wherein R is hydrogen, methyl or chlorine.

3. A process according to claim 2, wherein R is hydrogen.

4. A process according to claim 1, wherein $R_1$ and $R_2$ are, independently of the other, $C_1$-$C_{15}$alkyl or phenyl-$C_1$-$C_4$alkyl.

5. A process according to claim 5, wherein $R_1$ and $R_2$ are, each independently of the other, α,α-dimethylpropyl, benzyl, phenethyl, α-methylbenzyl and α,α-dimethylbenzyl.

6. A process according to claim 6, wherein $R_1$ and $R_2$ are, each independently of the other, α,α-dimethylpropyl, benzyl or α,α-dimethylbenzyl.

7. A process according to claim 6, wherein $R_1$ and $R_2$ are each α,α-dimethylpropyl.

8. A process according to claim 1, wherein 2-(2-hydroxy-3,5-di-tert-amyl-phenyl)- 2H-benzotriazole is prepared.

9. A process according to claim 1, wherein 2-[(2-hydroxy-3,5-di-(α,α-dimethylbenzyl)phenyl]- 2H-benzotriazole is prepared.

10. A process according to claim 1, wherein said hydrogenation catalyst is Raney-Ni, Ri, Pt, Pd or Pt/Pd.

11. A process according to claim 10, wherein said catalyst is Pt, Pd or Pt/Pd.

12. A process according to claim 1, wherein the hydrazine hydrate is employed in the range of about 50 to about 75%, relative to the molar amount of the o-nitroazobenzene compound of formula (II).

13. A process according to claim 12, wherein the hydrazine hydrate is employed in the range of about 55 to about 65%, relative to the molar amount of the o-nitroazobenzene compound of formula (II).

14. A process according to claim 1, wherein said hydrogenation catalyst is employed in the amount of about 0.1 to about 2%, relative to the weight of the o-nitroazobenzene compound of formula (II).

15. A process according to claim 14, wherein said hydrogenation catalyst is employed in the amount of about 0.3 to about 1.5%, relative to the weight of the o-nitroazobenzene compound of formula (II).

16. A process according to claim 15, wherein said hydrogenation catalyst is employed in the amount of about 0.5 to about 1.0%, relative to the weight of the o-nitroazobenzene compound of formula (II).

17. A process according to claim 1, wherein said organic base is an organic amine.

18. A process according to claim 17, wherein said organic amine is n-butylamine, diethylamine, pyrrolidone or pyridine.

19. A process according to claim 1, wherein said inorganic base is sodium hydroxide, potassium hydroxide, sodium carbonate, sodium bicarbonate, potassium carbonate, potassium bicarbonate, barium hydroxide or lithium hydroxide.

20. A process according to claim 19, wherein said inorganic base is sodium hydroxide.

21. A process according to claim 1, wherein said organic solvent is a $C_1$-$C_{14}$alcohol, optionally mixed with water, xylene, tetrahydrofuran or 2-butoxyethanol.

22. A process according to claim 21, wherein said organic solvent is a mixture of methanol/water.

23. A process according to claim 1, wherein the reaction of step (a) is carried out at a temperature of from about 20° to about 60° C.

24. A process according to claim 23, wherein the temperature is from about 25° to about 55° C.

25. An improved process for the preparation of an N-oxybenzotriazole compound of the formula III

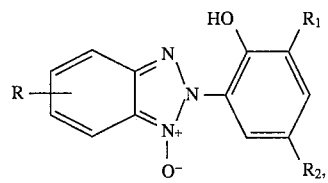

wherein
R is hydrogen, $C_1$-$C_{12}$alkyl, $C_1$-$C_4$alkoxy or halogen;
$R_1$ is hydrogen, $C_1$-$C_{24}$alkyl, $C_5$-$C_{12}$cycloalkyl, phenyl or phenyl-$C_1$-$C_9$alkyl;
$R_2$ is $C_1$-$C_{24}$alkyl, $C_5$-$C_{12}$cycloalkyl, phenyl, phenyl-$C_1$-$C_9$alkyl or a group —$C_nH_{2n}COOR_3$, in which n is 0 to 4 and $R_3$ is hydrogen or $C_1$-$C_{24}$alkyl or $R_2$ is —$(CH_2CH_2O)_xR_4$, in which x is 1 to 12 and $R_4$ is hydrogen or $C_1$-$C_{24}$alkyl, which process comprises the steps of a) catalytically reducing an azo compound of the formula II

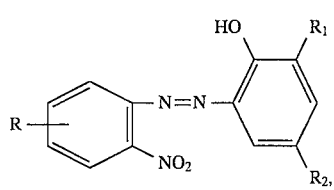

wherein R, $R_1$ and $R_2$ are as defined above, in the presence of an effective amount of hydrazine hydrate, a catalyst selected from the group consisting of Raney-Ni and the noble metals, an organic or inorganic base, an organic solvent, and optionally water, the reaction being carded out at temperatures between 15° and 60° C.

* * * * *